United States Patent
Amzaleg et al.

(10) Patent No.: US 10,290,092 B2
(45) Date of Patent: May 14, 2019

(54) SYSTEM, A METHOD AND A COMPUTER PROGRAM PRODUCT FOR FITTING BASED DEFECT DETECTION

(71) Applicant: Applied Materials Israel Ltd., Park Rabin (IL)

(72) Inventors: Moshe Amzaleg, Beer Sheva (IL); Nir Ben-David Dodzin, Hod Hasharon (IL)

(73) Assignee: APPLIED MATERIALS ISRAEL, LTD, Rehovot (IL)

(*) Notice: Subject to any disclaimer, the term of this patent is extended or adjusted under 35 U.S.C. 154(b) by 763 days.

(21) Appl. No.: 14/279,192

(22) Filed: May 15, 2014

(65) Prior Publication Data

US 2015/0332451 A1 Nov. 19, 2015

(51) Int. Cl.
*G06K 9/00* (2006.01)
*G06T 7/00* (2017.01)
*G01N 21/956* (2006.01)

(52) U.S. Cl.
CPC .......... *G06T 7/001* (2013.01); *G06T 7/0002* (2013.01); *G06T 7/0004* (2013.01); *G06T 7/0006* (2013.01); *G06T 7/0008* (2013.01); *G01N 2021/95615* (2013.01); *G06T 2207/20076* (2013.01); *G06T 2207/30148* (2013.01)

(58) Field of Classification Search
CPC ... G06T 7/0002; G06T 7/0004; G06T 7/0006; G06T 7/0008; G06T 7/001; G01N 21/88; G01N 21/8803; G01N 21/8806; G01N 21/9501; G01N 21/956; G01N 21/95607; G01N 2021/95615; G01R 31/308; G01R 31/309; G01R 31/311

USPC ........ 382/141, 144, 145, 147, 149, 150, 152
See application file for complete search history.

(56) References Cited

U.S. PATENT DOCUMENTS

| | | | |
|---|---|---|---|
| 5,153,444 A * | 10/1992 | Maeda | G06T 7/001 250/559.05 |
| 5,537,669 A * | 7/1996 | Evans | G06T 7/0004 382/141 |
| 5,659,172 A | 8/1997 | Wagner et al. | |
| 5,669,447 A | 9/1997 | Walker et al. | |
| 5,982,921 A | 11/1999 | Alumot et al. | |
| 6,178,257 B1 | 1/2001 | Alumot et al. | |
| 6,303,931 B1 * | 10/2001 | Menaker | G01N 23/04 250/307 |

(Continued)

FOREIGN PATENT DOCUMENTS

JP 05047886 A * 2/1993

*Primary Examiner* — Eric Rush
(74) *Attorney, Agent, or Firm* — Lowenstein Sandler LLP

(57) ABSTRACT

A system configured to detect defects in an inspection image generated by collecting signals arriving from an article, the system comprising a tangible processor which includes: (i) a distribution acquisition module, configured to acquire a distribution of comparison values, each of the comparison values being indicative of a relationship between a value associated with a pixel of the inspection image and a corresponding reference value; (ii) a fitting module, configured to fit to the distribution an approximation function out of a predefined group of functions; and (iii) a defect detection module, configured to: (a) set a defect detection criterion based on a result of the fitting; and to (b) determine a presence of a defect in the inspection image, based on the defect detection criterion.

23 Claims, 9 Drawing Sheets

(56) References Cited

U.S. PATENT DOCUMENTS

| | | | |
|---|---|---|---|
| 6,356,300 B1* | 3/2002 | Shiba | G06T 7/001 382/151 |
| 6,405,153 B1* | 6/2002 | Fiekowsky | G01N 21/956 702/159 |
| 6,621,571 B1* | 9/2003 | Maeda | G01N 21/9501 356/237.4 |
| 6,829,381 B2 | 12/2004 | Levin et al. | |
| 7,379,580 B2 | 5/2008 | Levin et al. | |
| 7,693,323 B2 | 4/2010 | Levin et al. | |
| 7,822,268 B2* | 10/2010 | Rothenfusser | G06T 7/0006 382/141 |
| 7,983,859 B2* | 7/2011 | Sato | G01R 31/2831 324/537 |
| 8,682,946 B1* | 3/2014 | Hiriyannaiah | G06F 17/18 708/200 |
| 2003/0145014 A1* | 7/2003 | Minch | G06F 17/30705 |
| 2004/0062432 A1* | 4/2004 | Ishikawa | G06T 7/001 382/145 |
| 2005/0121628 A1* | 6/2005 | Aoyama | G03F 1/36 250/492.22 |
| 2006/0159333 A1* | 7/2006 | Ishikawa | G06T 7/001 382/149 |
| 2007/0019861 A1* | 1/2007 | Zwanger | G06T 7/0002 382/171 |
| 2008/0249728 A1* | 10/2008 | Michelsson | G06T 7/0004 702/82 |
| 2009/0027664 A1* | 1/2009 | Hamamatsu | G01N 21/9501 356/237.5 |
| 2009/0037134 A1* | 2/2009 | Kulkarni | G01N 21/9501 702/127 |
| 2009/0046896 A1* | 2/2009 | Yamaguchi | G06K 9/4604 382/141 |
| 2009/0070049 A1* | 3/2009 | Ziegler | G01N 35/1016 702/50 |
| 2010/0131082 A1* | 5/2010 | Chandler | G06F 17/18 700/30 |
| 2010/0195437 A1* | 8/2010 | Bjerkholt | G01V 1/50 367/38 |
| 2015/0003721 A1* | 1/2015 | Pettibone | G06T 7/001 382/149 |
| 2015/0221076 A1* | 8/2015 | Gao | G06T 7/001 382/149 |

* cited by examiner

SYSTEM, A METHOD AND A COMPUTER PROGRAM PRODUCT FOR FITTING BASED DEFECT DETECTION

FIELD

This subject matter relates to systems, methods, and computer program products for defect detection.

BACKGROUND

Current demands for high density and performance associated with ultra large scale integration require submicron features, increased transistor and circuit speeds and improved reliability. Such demands require formation of device features with high precision and uniformity, which in turn necessitates careful process monitoring, including frequent and detailed inspections of the devices while they are still in the form of semiconductor wafers.

A conventional in-process monitoring technique employs a two phase "inspection and review" procedure. During the first phase, the surface of the wafer is inspected at high-speed and relatively low-resolution. The purpose of the first phase is to produce a defect map showing suspected locations on the wafer having a high probability of a defect. During the second phase the suspected locations are more thoroughly analyzed. Both phases may be implemented by the same device, but this is not necessary.

The two phase inspection tool may have a single detector or multiple detectors. Multiple detector two phase inspection devices are described, by way of example, in U.S. Pat. Nos. 5,699,447, 5,982,921, and 6,178,257 whose contents are hereby incorporated herein by reference.

The contents of U.S. Pat. Nos. 7,693,323; 6,829,381 and 7,379,580 are also hereby incorporated by reference.

There exists a need for improved and more robust techniques for detecting defects in articles, and especially in semiconductor substrates.

BRIEF DESCRIPTION OF THE DRAWINGS

In order to understand the subject matter and to see how it may be carried out in practice, embodiments will now be described, by way of non-limiting example only, with reference to the accompanying drawings, in which.

Figure 1:
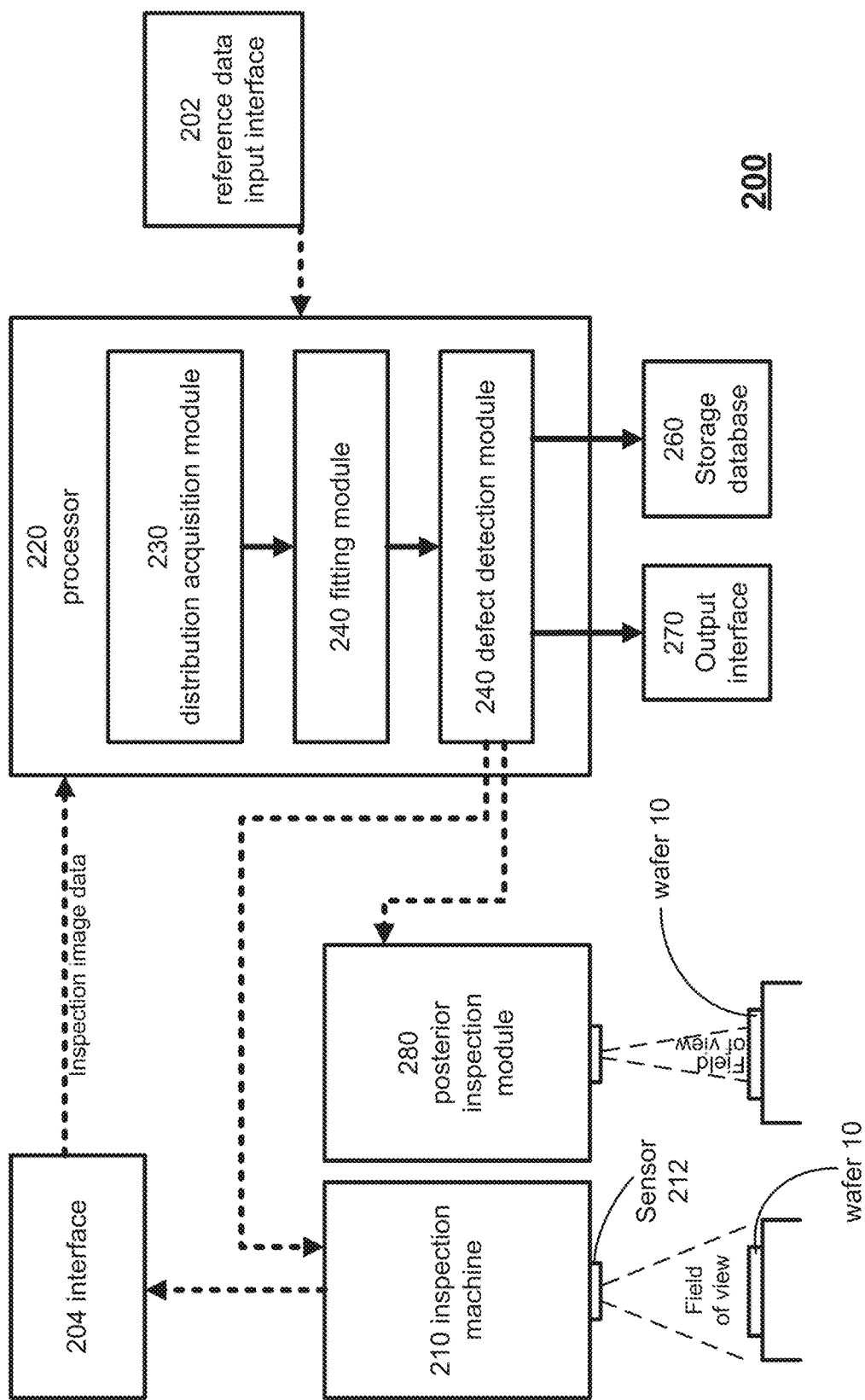
FIG. 1 is a block diagram of a system which is configured to detect defects in an inspection image generated by collecting signals arriving from an article, according to an embodiment of the subject matter.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

SUMMARY

In accordance with certain aspects of the presently disclosed subject matter, there is provided a method for computerized defect detection in an inspection image generated by collecting signals arriving from an article, the method including: (a) acquiring a distribution of comparison values, each of the comparison values being indicative of a relationship between a value associated with a pixel of the inspection image and a corresponding reference value; (b) fitting to the distribution an approximation function out of a predefined group of functions; (c) setting a defect detection criterion based on a result of the fitting; and (d) determining a presence of a defect in the inspection image, based on the defect detection criterion.

In accordance with certain embodiments of the presently disclosed subject matter, there is further provided a method, wherein the approximation function is a Parabola and the fitting includes selecting one or more Parabola parameters.

In accordance with certain embodiments of the presently disclosed subject matter, there is further provided a method, wherein the fitting includes selecting the approximation function by estimating errors between the distribution of comparison values and the approximation function.

In accordance with certain embodiments of the presently disclosed subject matter, there is further provided a method, wherein each of the comparison values is indicative of a difference between a color value of a pixel of the inspection image and a color value of a corresponding pixel of a reference image.

In accordance with certain embodiments of the presently disclosed subject matter, there is further provided a method, wherein the fitting gives smaller weight to common comparison values.

In accordance with certain embodiments of the presently disclosed subject matter, there is further provided a method, wherein the acquiring includes applying an operator to values of the distribution, wherein for at least half of values of the distribution, a difference between an output value of the operator and $MAX(\log(x), \text{const})$ is less than 10% of a maximum value of the distribution.

In accordance with certain embodiments of the presently disclosed subject matter, there is further provided a method, wherein the outputs of the approximation function for comparison values whose distance from the average comparison value is larger than the standard deviation of the distribution are bound between a higher limit and a lower limit, wherein a difference between the higher and lower limits is smaller than 5% of the maximum value of the distribution.

In accordance with certain embodiments of the presently disclosed subject matter, there is further provided a method, wherein the fitting gives smaller weight to comparison values whose distance from an average comparison value is larger than a standard deviation of the distribution.

In accordance with certain embodiments of the presently disclosed subject matter, there is further provided a method, wherein the fitting gives smaller weight to: (a) common comparison values, and to (b) comparison values whose distance from an average comparison value is larger than a standard deviation of the distribution.

In accordance with certain embodiments of the presently disclosed subject matter, there is further provided a method, wherein the setting includes determining a threshold, wherein the determining includes comparing to the threshold a difference between a color value of a pixel of the inspection image and a color value of a corresponding pixel of a reference image, wherein the determining of the presence of the defect is based on a result of the comparing.

In accordance with certain aspects of the presently disclosed subject matter, there is yet further provided a system that is configured to detect defects in an inspection image generated by collecting signals arriving from an article, the system including a tangible processor which includes: (i) a distribution acquisition module, configured to acquire a distribution of comparison values, each of the comparison values being indicative of a relationship between a value associated with a pixel of the inspection image and a corresponding reference value; (ii) a fitting module, configured to fit to the distribution an approximation function out of a predefined group of functions; and (iii) a defect detection module, configured to (a) set a defect detection criterion based on a result of the fitting; and to (b) determine a presence of a defect in the inspection image, based on the defect detection criterion.

In accordance with certain embodiments of the presently disclosed subject matter, there is yet further provided a system, wherein the approximation function is a Parabola and the fitting module is configured to select one or more Parabola parameters.

In accordance with certain embodiments of the presently disclosed subject matter, there is yet further provided a system, wherein the fitting module is configured to select the approximation function by estimating errors between the distribution of comparison values and the approximation function.

In accordance with certain embodiments of the presently disclosed subject matter, there is yet further provided a system, wherein each of the comparison values is indicative of a difference between a color value of a pixel of the inspection image and a color value of a corresponding pixel of a reference image.

In accordance with certain embodiments of the presently disclosed subject matter, there is yet further provided a system, wherein the fitting module is configured to give smaller weight to common comparison values when fitting the approximation function to the distribution.

In accordance with certain embodiments of the presently disclosed subject matter, there is yet further provided a system, wherein the distribution acquisition module is configured to apply an operator to values of the distribution, wherein for at least half of values of the distribution, a difference between an output value of the operator and MAX(log(x), const) is less than 10% of a maximum value of the distribution.

In accordance with certain embodiments of the presently disclosed subject matter, there is yet further provided a system, wherein the outputs of the approximation function for comparison values whose distance from the average comparison value is larger than the standard deviation of the distribution are bound between a higher limit and a lower limit, wherein a difference between the higher and lower limits is smaller than 5% of the maximum value of the distribution.

In accordance with certain embodiments of the presently disclosed subject matter, there is yet further provided a system, wherein the fitting module is configured to give smaller weight to comparison values whose distance from an average comparison value is larger than a standard deviation of the distribution when fitting the approximation function to the distribution.

In accordance with certain embodiments of the presently disclosed subject matter, there is yet further provided a system, wherein the fitting module is configured to give smaller weight to: (a) common comparison values, and to (b) comparison values whose distance from an average comparison value is larger than a standard deviation of the distribution, when fitting the approximation function to the distribution.

In accordance with certain embodiments of the presently disclosed subject matter, there is yet further provided a system, wherein the defect detection module is configured to set the defect detection criteria by setting a threshold, to compare to the threshold a difference between a color value of a pixel of the inspection image and a color value of a corresponding pixel of a reference image, and to determine the presence of the defect based on a result of the comparing.

In accordance with certain aspects of the presently disclosed subject matter, there is yet further provided a non-volatile program storage device readable by machine, tangibly embodying a program of instructions executable by the machine to perform a method for defect detection in an inspection image generated by collecting signals arriving from an article including: (a) acquiring a distribution of comparison values, each of the comparison values being indicative of a relationship between a value associated with a pixel of the inspection image and a corresponding reference value; (b) fitting to the distribution an approximation function out of a predefined group of functions; (c) setting a defect detection criterion based on a result of the fitting; and (d) determining a presence of a defect in the inspection image, based on the defect detection criterion.

In accordance with certain embodiments of the presently disclosed subject matter, there is yet further provided a program storage device, wherein the approximation function is a Parabola and the fitting includes selecting one or more Parabola parameters.

In accordance with certain embodiments of the presently disclosed subject matter, there is yet further provided a program storage device, wherein the fitting includes selecting the approximation function by estimating errors between the distribution of comparison values and the approximation function.

In accordance with certain embodiments of the presently disclosed subject matter, there is yet further provided a program storage device, wherein each of the comparison values is indicative of a difference between a color value of a pixel of the inspection image and a color value of a corresponding pixel of a reference image.

In accordance with certain embodiments of the presently disclosed subject matter, there is yet further provided a program storage device, wherein the fitting gives smaller weight to common comparison values.

In accordance with certain embodiments of the presently disclosed subject matter, there is yet further provided a program storage device, wherein the acquiring includes applying an operator to values of the distribution, wherein for at least half of values of the distribution, a difference between an output value of the operator and MAX(log(x), const) is less than 10% of a maximum value of the distribution.

In accordance with certain embodiments of the presently disclosed subject matter, there is yet further provided a program storage device, wherein the outputs of the approximation function for comparison values whose distance from the average comparison value is larger than the standard deviation of the distribution are bound between a higher limit and a lower limit, wherein a difference between the higher and lower limits is smaller than 5% of the maximum value of the distribution.

In accordance with certain embodiments of the presently disclosed subject matter, there is yet further provided a program storage device, wherein the fitting gives smaller weight to comparison values whose distance from an average comparison value is larger than a standard deviation of the distribution.

In accordance with certain embodiments of the presently disclosed subject matter, there is yet further provided a program storage device, wherein the fitting gives smaller weight to: (a) common comparison values, and to (b) comparison values whose distance from an average comparison value is larger than a standard deviation of the distribution.

In accordance with certain embodiments of the presently disclosed subject matter, there is yet further provided a program storage device, wherein the setting includes determining a threshold, wherein the determining includes comparing to the threshold a difference between a color value of a pixel of the inspection image and a color value of a corresponding pixel of a reference image, wherein the determining of the presence of the defect is based on a result of the comparing.

DETAILED DESCRIPTION OF EMBODIMENTS

In the following detailed description, numerous specific details are set forth in order to provide a thorough understanding of the subject matter. However, it will be understood by those skilled in the art that the present subject matter may be practiced without these specific details. In other instances, well-known methods, procedures, and components have not been described in detail so as not to obscure the present subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "processing", "calculating", "determining", "generating", "setting", "configuring", "selecting", "defining", "computing" or the like, include action and/or processes of a computer that manipulate and/or transform data into other data, said data represented as physical quantities, e.g. such as electronic quantities, and/or said data representing the physical objects. Terms such as "computer", "processor", "processing module", "processing unit", and the like should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

In embodiments of the presently disclosed subject matter one or more stages illustrated in the figures may be executed in a different order and/or one or more groups of stages may be executed simultaneously and vice versa. The figures illustrate a general schematic of the system architecture in accordance with an embodiment of the presently disclosed subject matter. Each module in the figures can be made up of any combination of software, hardware and/or firmware that performs the functions as defined and explained herein. The modules in the figures may be centralized in one location or dispersed over more than one location.

The presently disclosed subject matter is useful, among other applications, for the detection of defects during the fabrication of integrated circuits and other microdevices. In the following, embodiments of the subject matter will be described with reference to the detection of defects on wafers. While the term wafer may be used to refer only to the substrate material on which the integrated circuit is fabricated (e.g. a thin slice of semiconductor material, such as a silicon crystal), this term may also be used to refer to the entire construction, including the electronic circuit fabricated on the wafer. Typically, wafers are divided into multiple dies. Like the term 'wafer', the term 'die' may also be used either for small blocks of semiconducting material, on which a given functional circuit is fabricated, or for such a block including the fabricated electric circuit. Usually, wafers may be cut ("diced") into its multiple dies wherein all of the dies of the wafer contain a copy of the same electronic circuit. While not necessarily so, each of the dies is independently functional. A single die may include a large amount of patterns that well exceed millions of patterns per die. It should be noted that the subject matter is not limited to multiple dies wafers and can be useful for single die wafers as well. Further, the subject matter is useful for the detection of defects on masks and reticles and other semiconductor devices and other devices.

A semiconductor die usually includes a plurality of layers. A pattern may be a part of a metal interconnection line, a trench, a via, a conductive gate, etc. Different areas on each die may be put to different uses; such areas may be for example background areas (that are ideally very smooth), memory areas (that include a large number of repetitive patterns) and logic areas (that usually do not include large quantities of adjacent repetitive patterns).

FIG. 1 is a block diagram of system 200 which is configured to detect defects in an inspection image generated by collecting signals arriving from an article (such as article 10), according to an embodiment of the subject matter. System 200 includes at least tangible processor 220 (which in turn includes several modules which may be operated for defect detection), but may include additional components such as any combination of components 204, 210, 270, 280 and 290. Processor 220 includes several modules (which may be implemented in software, hardware, firmware, or any combinations of the above) which operate for processing inspection results which are based on an inspection image, to detect defects in an article which is imaged in that image. Before processor 220 is discussed in greater detail, however, the inspection system will be described in more detail. While not necessarily so, article 10 may be selected from a group consisting of an electronic circuit, a wafer, a reticle, and a photomask.

System 200 may obtain the inspection image in many ways. For example, system 200 may be combined with an inspection machine 210 that is used to inspect the wafer or other types of articles (e.g. during different stages of manufacturing thereof). In another implementation system 200 may be connected to such an inspection machine, or the inspection image may be transmitted by an off-line device connected to only one of the machines at a time. Also, system 200 may be an inspection machine into which some or all of the modifications and/or features discussed below have been integrated.

The inspection system may be, for example, any out of the many detection tools which are known in the art such as having single detector, multiple detectors, dark field detectors, bright field detectors or any combination of detectors. Alumot system is a multi detector system but other multi-detector systems having other arrangements of detectors may be implemented.

Without limiting the scope of the subject matter in any way, in some possible implementations system 200 may be used for inspection tools in which an entire wafer or at least an entire die is scanned for detection of potential defects (such as the Elite and the UVision systems by Applied Materials, Inc.), and/or for review tools which are typically of higher resolution (e.g. a scanning electron microscope, SEM) which are used for ascertaining whether a potential defect is indeed a defect. Such review tools usually inspect fragments of a die, one at a time, in high resolution. Whenever the term "inspection" or its derivatives are used in this disclosure, such an inspection is not limited with respect to resolution or size of inspection area, and may be applied, by way of example, to review tools and to lower resolution wafer inspection tools alike.

While not necessarily so, the process of operation of system 200 may correspond to some or all of the stages of method 500 (described below). Likewise, method 500 and its possible implementations may possibly be implemented by a system such as system 200. It is therefore noted that embodiments of the subject matter discussed in relation to method 500 may also be implemented, mutatis mutandis, in a hardware counterpart as various embodiments of system 200, and vice versa.

It should be noted that, as will be clear to any person who is of skill in the art, wherever the term "wafer" is used—similar techniques, systems, methods and computer program products may be implemented for optical masks that are used for the manufacturing of wafers.

The scanning of the article 10 may be implemented by any scanning, imaging and/or detecting apparatus, many of which are known in the art. Such an apparatus (denoted "sensor 212") may be part of system 200, but this is not necessarily so and the two may or may not be directly connected. By way of example, such an apparatus may be a scanning electron microscope, an optical inspection system and so forth.

By way of example, a wafer 10 (or several wafers, or one or more articles of another type) may be placed on a movable stage. In such an implementation, article 10 remains stationary with respect to the movable stage during the scanning of the article, and the respective movement between the article 10 and sensor 212 (if required to image different parts of the article) is achieved by controllably moving the movable stage. For example, the movable stage may be moved along an X-axis, a Y-axis, and possibly also a Z-axis direction (wherein the X and Y axes are perpendicular axes on the surface plane of the movable stage, and the Z-axis is perpendicular to both of these axes). Alternatively (or in addition), sensor 212 may change a position in order to image different parts of article 10.

In inspection machine 210, a portion of article 10 is illuminated by a beam 214 transmitted by illumination module (in the illustrated example, the illumination module is combined in a co-axial way with sensor 212). Such a beam 214 may be a beam of light (e.g. visible light, infrared light, ultraviolet light, and so on, e.g. a laser), a beam of another kind of electromagnetic radiation (e.g. radio waves, microwaves, X-rays, Gamma rays, etc.), a beam of particles (e.g. a beam of electrons), and so on.

The illumination beam 214 interacts with the portion of article 10, and outgoing signals which are a result of such interaction may then be captured by one or more sensors 212. Different types of such interactions may occur when the illumination beam meets the article. For example, parts of the illumination beam may be reflected towards such a sensor 212, parts of the illumination beam may be deflected towards such a sensor 212, parts of the illumination beam may be diffracted towards such a sensor 212, parts of the illumination may result in emission of another type of radiation/particles towards such a sensor, and so on. For the sake of simplicity, only one sensor 212 is illustrated, which captures reflected signals from the article 10.

Tangible processor 220 includes distribution acquisition module 230, which is configured to acquire a distribution of comparison values, each of the comparison values being indicative of a relationship between a value associated with a pixel of the inspection image (also equivalently referred to herein as "inspected value of the inspection image") and a corresponding reference value (also equivalently referred to herein as "corresponding value of a reference image"). The inspection image was generated by collecting signals arriving from a portion of the article which includes the part. For example, the inspection image may be generated by inspection machine 210, and later processed by acquisition module 230 to provide the distribution. It is noted that optionally, the article is selected from a group consisting of a wafer, a reticle, a photomask, and an electric circuit.

Alternatively, the processing of the inspection image to provide the distribution may be executed by an intermediate unit operative between the inspection machine 210 and distribution acquisition module 230, or even by inspection machine 210. Even in such a case, the distribution attribution module may further process the distribution (e.g. by logging the values of the distribution).

Optionally, distribution acquisition module 230 may be configured to apply an operator to values of the distribution, wherein for at least half of values of the distribution, a difference between an output value of the operator and an output value of a log function is less than 10% of a maximum value of the distribution.

Optionally, distribution acquisition module 230 may be configured to apply an operator to values of the distribution, wherein for at least half of values of the distribution, a difference between an output value of the operator (for a selected value out of the at least half of the values of the distribution) and a result of a maximum function whose inputs are: (a) an output value of a log function (applied to the selected value), and (b) a constant value, is less than 10% of a maximum value of the distribution.

That is, optionally, distribution acquisition module 230 may be configured to apply an operator to values of the distribution, wherein for at least half of values of the distribution, a difference between an output value of the operator W(x) (for a selected value x) and MAX(log(x), const) is less than 10% of a maximum value of the distribution. For example, the constant const may be equal to zero (const=0).

Each of the comparison values may be indicative of a difference between a value associated with a pixel of the inspection image (e.g. color value such as grey level value) and a corresponding reference value (e.g. color value such as grey level value). The value associated with a given pixel of the inspection image may pertain only to that pixel (e.g. color value of that pixel), but this is not necessarily so (e.g. it may be an average of the color values of more than one pixel, it may be a variance value—i.e. the difference between the color value of the brightest pixel in an area surrounding that pixel to the color value of the darkest pixel in that area, and so on). For any comparison value, the corresponding reference value may represent one corresponding pixel of one reference image, may represent more than one corresponding pixels in one reference image, and/or may represent one or more corresponding pixel(s) in each of a plurality of reference images.

Acquisition module 230 may receive the inspection image and/or the comparison values and/or the distribution (depending on where the processing of the inspection image is done) using one or more tangible interface 204 modules (e.g. over cable connection, or by one or more wireless connection devices).

Examples of ways in which acquisition module 230 may operate are discussed in further detail in relation to stages 510, 520, 530 and 531 of method 500. It is noted that distribution acquisition module 230 may execute any of the to be discussed variations of stages 510, 520, 530 and/or 531, even if not explicitly elaborated.

Processor 220 further includes fitting module 240, which is configured to fit to the distribution an approximation function out of a predefined group of functions. The family of functions may be defined by fitting module 240, or externally to it (e.g. by an external system, by a human, and so on). Fitting module 240 may implement various techniques to fit the approximation function to the inspection results. For example, it may minimize an error estimation function such as a standard least mean squared (LMS) function between the approximation function and the distribution.

Fitting module 240 may also apply weighted error estimation functions, thereby giving different weights to different comparison values. For example, fitting module 240 may be configured to utilize an error estimation function which gives smaller weight to common comparison values (e.g., instead of Σ(Nestimation(Fj),Di−Nactual,Di)2 as suggested below, the error estimation function (which is later minimized) may be Σ(1/Nestimation(Fj),Di)·(Nestimation(Fj), Di−Nactual,Di)2).

Alternatively (or additionally), fitting module 240 may be configured to utilize an error estimation function which gives smaller weight to difference values whose distance from an average difference value is relatively large (e.g. larger than the standard deviation). For example, instead of Σ(Nestimation(Fj),Di−Nactual,Di)2 as suggested below, the error estimation function (which is later minimized) may be Σ(1/Di)·(Nestimation(Fj),Di−Nactual,Di)2.

Examples of ways in which fitting module 240 may operate are discussed in further detail in relation to stages 540, 541, 542, and 543 of method 500. It is noted that fitting module 240 may execute any of the to be discussed variations of stages 540, 541, 542 and/or 543, even if not explicitly elaborated.

Optionally, fitting module 240 may be configured to give smaller weight to common comparison values when fitting the approximation function to the distribution.

Optionally, fitting module 240 may be configured to give smaller weight to comparison values whose distance from an average comparison value is larger than a threshold (e.g. larger than a standard deviation of the distribution) when fitting the approximation function to the distribution. It is noted that optionally the threshold may be a predetermined threshold, but this is not necessarily so.

Optionally, fitting module 240 may be configured to give smaller weight to: (a) common comparison values, and to (b) comparison values whose distance from an average comparison value is larger than a threshold (e.g. larger than a standard deviation of the distribution), when fitting the approximation function to the distribution.

Optionally, the outputs of the approximation function for comparison values whose distance from the average comparison value is larger than a threshold (e.g. larger than the standard deviation of the distribution) are bound between a higher limit and a lower limit, wherein a difference between the higher and lower limits is smaller than 5% of the maximum value of the distribution.

Processor 220 further includes defect detection module 250, which is configured to (a) set a defect detection criterion based on a result of the fitting; and to (b) determine a presence of a defect in the inspection image, based on the defect detection criterion. More generally, module 250 may be configured to classify pixels of the inspection image, based on compliance of the comparison values associated with these pixels with a criterion it sets based on the result of the fitting.

Examples of ways in which defect detection module 250 may operate are discussed in further detail in relation to stage 550 of method 500. It is noted that defect detection module 250 may execute any of the to be discussed variations of stage 550, even if not explicitly elaborated.

For example, defect detection module 250 may be configured to set the defect detection criteria by setting a threshold, to compare to the threshold a difference between a color value associated with a pixel of the inspection image and a corresponding color reference value, and to determine the presence of the defect based on a result of the comparing.

System 200 may include a tangible storage 260 (e.g. a hard-drive disk, a flash drive, etc.) for storing the results of the defect detection (and possibly of additional information pertaining to the defective pixels) to a tangible storage. System 200 may also include an output interface 270 for transmitting such information to an external system (e.g.

over cable connection or over wireless connection), wherein that external system may in turn act based on the classification.

System 200 may also include an inspection module, which may be the aforementioned inspection machine 210 which provides the aforementioned inspection image by scanning of the inspected articles such as the wafers, and may alternatively be posterior inspection module 280 that is configured to inspect the wafer (or other inspected article) in higher resolution than that of the inspection image. This inspection module may be configured to selectively scan, in a resolution higher than the resolution of the inspection image, parts of the inspected article in which a defect is determined to be present, as determined by defect detection module 250. The field of view of posterior inspection module 280 may be narrower than that of inspection machine 210, but this is not necessarily so.

It should be noted that inspection machine 210 and/or posterior inspection module 280, if implemented, may be implemented as inspection machines of various types, such as optical imaging machines, electron beam inspection machines, radars, LIDARs and so on.

Generally, identifying defects in a wafer (or in another inspected article) may be implemented using different techniques, among which are optical inspection and electron beam inspection. Utilization of system 200 may facilitate the use of more than a single inspection technique. For example, an initial inspection of the wafer is firstly carried out relatively quickly and in a coarse manner by inspection system 200 (e.g. using an optical inspection or an electron beam inspection set for coarse and fast inspection). Later, some of the potential defects found in the initial inspection (selected based on the results of defect detection module 250) are then studied again using a relatively slower but more exact inspection. Such posterior scanning may be executed either in another mode of inspection machine 210, or in a different posterior inspection module 280 (in a process also referred to as "reviewing", e.g. by DRSEM—Defect Review Scanning Electron Microscope).

Figure 2:
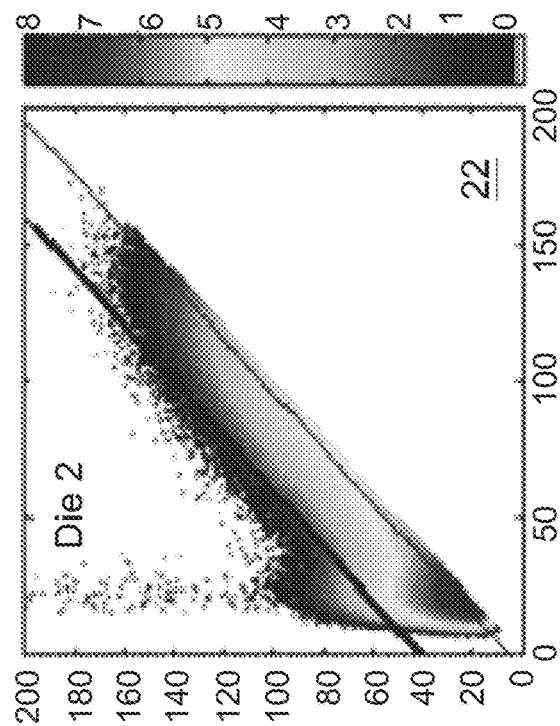
FIG. 2 includes graphs which refer to comparisons between pixels of a compared die in an inspected article to corresponding pixels of a reference die.
Figure 2:
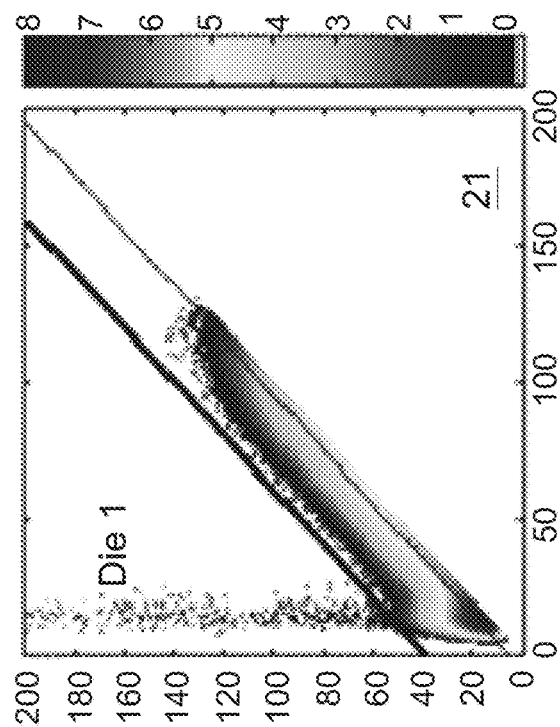

FIG. 2 includes two graphs, 21 and 22, each of which refers to a comparison between pixels of a compared die in an inspected article (in this case, a wafer), to corresponding pixels of a reference die (in a pixel-to-pixel comparison). The comparison is a comparison of the color value (in this case—the gray level (GL) values) of the pixels. In each comparison (that illustrated in graph 21 and that illustrated in graph 22), a pixel from the scanned die—die 1 or die 2—and a pixel from a reference die are compared. The comparison is shown in absolute value (i.e. out of each pair of pixels, the one having lower GL is represented on the abscissa, and the one having higher GL is represented on the ordinate), where the shade of gray in each of the positions on the graph represents the number of pairs of pixels which have the values indicated by the abscissa and the ordinate of the graph.

As can be seen, substantially all of the pairs of pixels in which the GL of both pixels of the pair is higher than 50 (denoted by abscissa values) in the comparison of graph 21 have a difference of less than 40 GL grades (this is illustrated by the diagonal line crossing the ordinate at 40). However, in graph 22, there are a large number of pairs whose GL difference is significantly larger than 40 (the dots above the line crossing the ordinate at 40). Therefore, a threshold that would be useful for detecting unusual differences for die 1, would be inadequate for die 2.

For example, process variations may affect the local compare histogram. In manufacturing of electrical wafers, such process variation may be noticed in transition between lots, wafers and dies. Such process variation may cause an unstable detection (Higher false alarm rate (FAR)). Assuming that each pixel of the inspection image is to be compared to exactly one corresponding reference pixel in one reference image, defects in an inspection image may be detected by comparing the inspection image to the reference image on a pixel-to-pixel basis. This may be achieved by comparing an inspected value which is representative of a target pixel of the inspection image (e.g. its color value (such as gray-level value), number of photons, radiation level, and any value based on such characteristics) to the inspected value which is representative of a corresponding reference pixel of the reference image. The reference pixel may be selected, in accordance with known methods, based on the locations of the target pixel and of the reference pixel with respect to the corresponding image, and/or based on locations associated with those pixels with respect to locations on an inspected object that is inspected in at least one of the images (the other image may be of the same object, but not necessarily so, e.g. it may be an image of a similar object or a computer aided design (CAD) based image).

In some examples described herein it is assumed that each pixel of the inspection image is compared to exactly one corresponding reference pixel in one reference image and therefore the corresponding reference value represents one reference pixel in one reference image. If this is not the case, processing of one or more of the images may yield an equivalent scenario. For instance, the corresponding reference value may be a statistically generated value representing more than one reference image and/or more than one corresponding reference pixel. Therefore this assumption will be pursued, in order to keep the explanations below as clear and terse.

A result of a comparison (the "comparison value") is indicative of the relationship between a value associated with a pixel of the inspection image and a corresponding reference value. For simplicity it will be assumed that the comparison value is the difference between two numeric values (e.g. difference of gray levels), i.e. a subtraction of one of these values from the other. It is however noted that other kinds of relationships may be reflected in the comparison value—e.g. a ratio between the two values, a logarithm of the difference or the ratio, and so on. The comparison value may be indicative of how different are the values from one another. See also, for example, the description of 520 below.

A large difference between a value associated with a pixel of the inspection image and a corresponding reference value may result from a defect in (at least) one of the represented pixels (i.e. in area of the inspected article which is imaged in that pixel), but may also result from other factors such as noise, difference in overall illumination level of the images, and so forth. Therefore, a threshold of acceptable comparison values may be determined (for the entire inspection image or for different subgroups of pixels). Pixels of the inspection image for which a comparison value which exceeds the threshold is determined may be regarded as defective (or at least as having a possible defect), while others may be regarded as normal. Criteria other than (and possibly equivalent) to the comparison to a threshold may also be implemented, as discussed below.

The techniques discussed herein may be used to determine such a threshold (or another parameter for analyzing comparison values based on which), based on a fitting of comparison values distribution data (which is based on comparison values determined for various pixels of the inspection image) to a model function, and then determining the threshold based on the selected model function.

Figure 3:
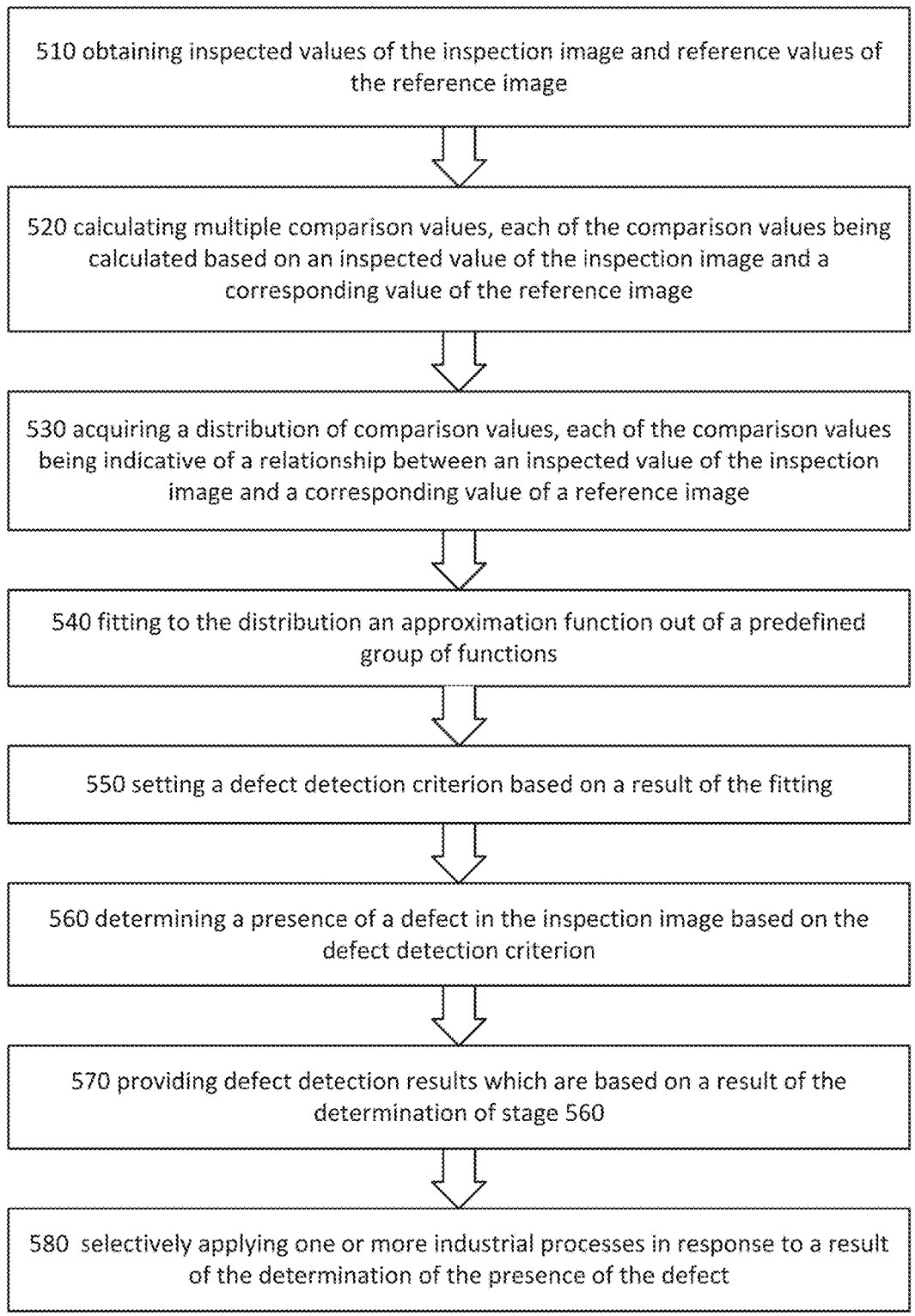
FIGS. 3, 4, 6, and 9 are flowcharts describing a method for computerized defect detection in an inspection image generated by collecting signals arriving from an article, according to various embodiments of the subject matter.

FIG. 3 is a flowchart of method 500 for computerized defect detection in an inspection image generated by collecting signals arriving from an article, according to an embodiment of the subject matter. Referring to the examples set forth in other drawings, method 500 may be carried out by system 200. Different embodiments of system 200 may implement the various disclosed variations of method 500 even if not explicitly elaborated. Likewise, different embodiments of method 500 may include stages whose execution fulfills the various disclosed variations of system 200, even if succinctness and clarity of description did not necessitate such repetition.

Method 500 may be implemented for various types of inspected objects, from a very minute scale (e.g. millimetric or nanoscale objects) to larger objects such as geographical area imaged from an airplane or from a satellite. In order to clarify the disclosure, different stages of method 500 will be exemplified using an example of an inspected object which is selected from a group consisting of an electronic circuit, a wafer, a reticle and a photomask (a partially transparent plate which may be used for the manufacturing of electronic circuits or other objects in a process implementing transmitting light through such a photomask, such as photolithography).

It is noted that while method 500 is described as a method for detecting defects (or at least potential defects) in an inspected article, a person who is of ordinary skill in the art would understand that method 500 may equivalently be implemented for detection of many other types of items within various types of inspection images. For example, apart from deviations from an expected pattern (such as a hole in a textile fabric, or a potential manufacturing defect in a wafer), other kinds of items which may be identified are specific items or a group thereof (e.g. looking for tanks in aerial images or for intruders in security camera data).

Stage 530 of method 500 includes acquiring a distribution of comparison values, each of the comparison values being indicative of a relationship between a value associated with a pixel in the inspection image and a corresponding reference value. Such a relationship may be the difference (i.e. subtraction) between a value associated with the pixel in the inspection image (e.g. color value) and the corresponding reference value, or the absolute value of such a subtraction. However, other types of relationships may be reflected in the comparison values, (as described elsewhere herein). The value associated with a given pixel in the inspection image may pertain to that single pixel, but this is not necessarily so, as discussed above. Likewise, the corresponding reference value may be the value (e.g. color value) of a single pixel of the reference image, but this is not necessarily so, as discussed above. It is noted that a reference image may also be an inspection image, but may also be otherwise obtained—e.g. from CAD data. Referring to the examples set forth with respect to other drawings, stage 530 may be carried out by an acquisition module such as distribution acquisition module 230.

Optionally, each of the comparison values may be indicative of a difference between a color value of a pixel of the inspection image and a color value of a corresponding pixel of the reference image.

The distribution may be acquired in several ways, possibly also from an external source or system. One of the ways in which the distribution may be acquired is by executing stages 510 and 520.

Stage 510 of method 500 includes obtaining values associated with pixels of the inspection image and reference values. Referring to the examples set forth with respect to other drawings, stage 510 may be carried out by an inspection machine such as inspection machine 210, and/or by an inspection result interface such as inspection results interface 204 of system 200.

A value associated with a pixel of the inspection image (and likewise a reference value, in the following discussion) may be simply a color-value, or a color-based attribute which is based on the color-value, but this is not necessarily so. When associated with a gray-level (GL) image, the value may be the one-dimensional color value. When associated with a color image, the value may be a one-dimensional color value in one out of multiple color channels (e.g. Red, Green, or Blue, in an RGB image), an intensity value, a color identifier, and so on.

Figure 9:
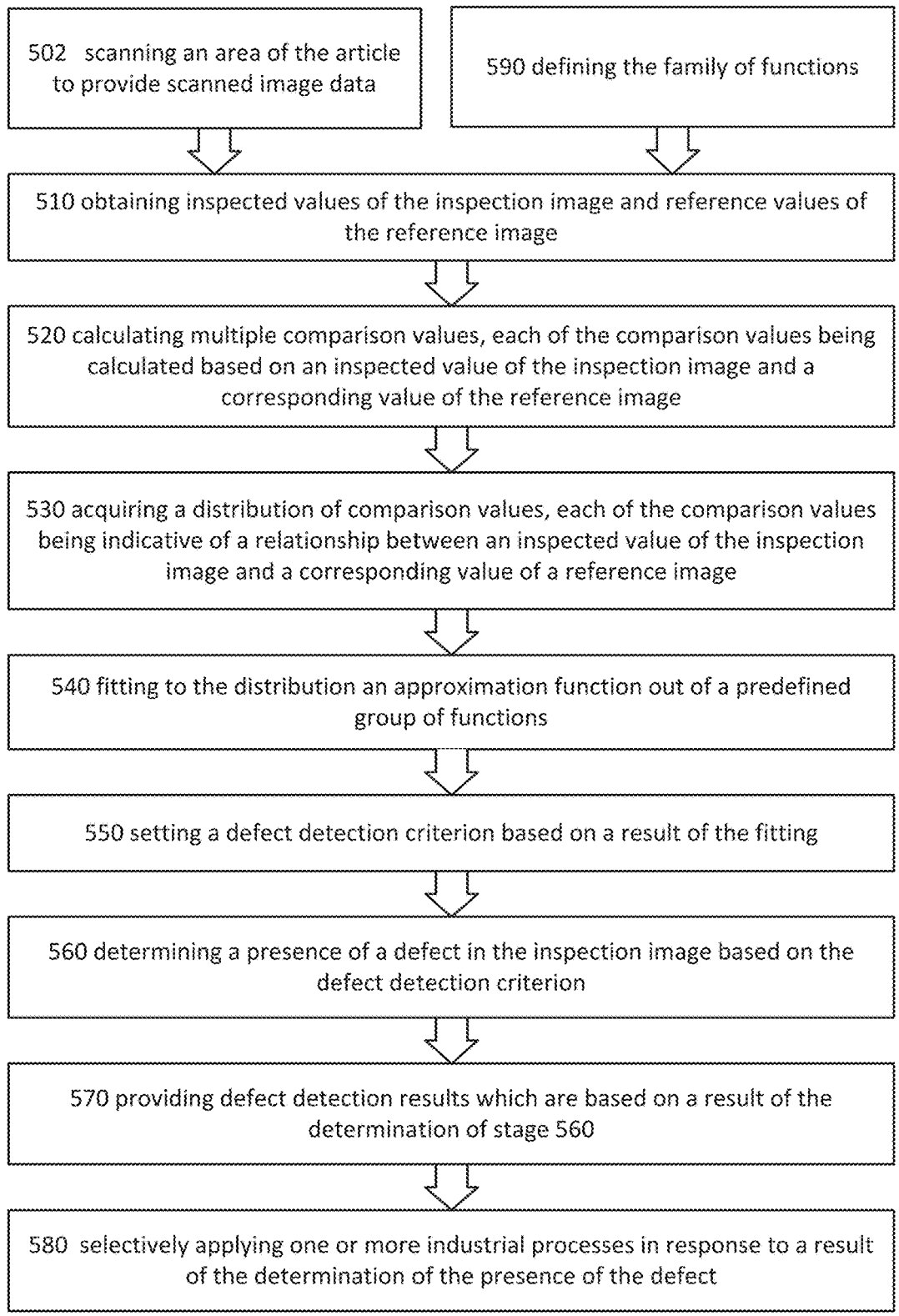

The obtaining may include obtaining such information from an external system (e.g. from an external inspection unit, external camera or detector, and so on), and/or obtaining such information by capturing (or otherwise generating) the aforementioned pixel information, and possibly the inspection image itself. Method 500 may include a stage of capturing the image information (e.g. as part of a scanning of the inspected object). Various possible implementations of the capturing of the pixel information are discussed with respect to optional stage 502, which is illustrated in FIG. 9.

An inspection image may be based on information acquired by one or more out of a wide range of detector types, such as optical camera, scanning electronic microscope, laser detector, RADAR, sonar, and so on. A reference image may be an image of the same inspected object (e.g. the same or another die of a wafer), an image of a different object (e.g. similar die from another wafer of the batch), or an image manufactured by a machine (e.g. from CAD database, from one or more other images, etc.).

The acquiring may include the inspection itself (e.g. inspecting the inspected object by a camera, by a scanning electron microscope, by a RADAR, etc.), and may include receiving the inspection image and/or the reference image(s) from an external unit. Also, as mentioned above in the following discussion it is assumed that the reference image (s) cover(s) substantially the same area as the inspection image. However, the method may be easily adapted to situations in which this is not the case, and such adaptations are included within the scope of the subject matter, even if the discussion of which is limited for reasons of clarity and brevity.

The inspection image and the reference image(s) may be taken by the same inspection machine, but this is not necessarily so. The classification of pixels may be used for detection of changes between the pixels, such as for finding defects in an electronic circuit (e.g. imprinted on a wafer), for finding changes between images of a security camera, and so on.

Step 520 of method 500 includes calculating multiple comparison values, each of the comparison values being calculated based on a value associated with a pixel in the inspection image and a corresponding reference value, and being indicative of a relationship between the two. For instance, stage 520 may include comparing the value (e.g. GL value) of each out of multiple pixels of the inspection image to the respective corresponding reference value (e.g. GL value). Referring to the examples set forth with respect to other drawings, stage 520 may be carried out by an acquisition module such as distribution acquisition module 230.

For example, stage 520 may include calculating difference values for various pixel pairs, each pair including a compared pixel from the inspection image, and a reference pixel from a reference image (e.g. each pixel of the pair having the same (x,y) location within the respective image as the other pixel of the pair). Difference values may be calculated for any portion of the inspection image (e.g. the portion may include all the pixels of the inspection image, all the pixels of a given area of the inspection image, or any other subset of the pixels of the inspection image). For example, the pixels of the inspection image may be divided to noise-based population (e.g. based on variance thresholds), and the distribution may only pertain to pixels of one (or some) of the noise populations, but not to pixels which belong to other one or more noise populations.

The calculated difference may be a result of subtraction of the value associated with the pixel in the inspection image from the corresponding reference value (or vice versa), the absolute value of such subtraction, a result of a function which is based on either of those results (e.g. the rounding up of the absolute value), or another function. Any of the above suggested values may pertain to either scalar values (e.g. gray-level or intensity) or to vector values (e.g. an (R,G,B) color triplet). While the calculated difference may be a numerical difference (e.g. a result of subtraction), it may also be of another type (such as a classification e.g. [small, medium, large], etc.). See also, for example, the description above regarding possible comparison values.

The description now reverts to stage 530 which includes acquiring the distribution of the comparison values. In stage 520 (if executed), comparison values were calculated for multiple pairs of values (each pair including a value pertaining to a pixel in a portion of the inspection image and a corresponding reference value). A distribution of the comparison values may therefore be determined based on such data. For each of various comparison values (possibly for all of them), the distribution is indicative of the amount of pixels in the portion of the inspection image for which that comparison value was computed. For example, the distribution may be represented as a histogram, as a table, and so on.

Stage 540 includes fitting to the distribution an approximation function out of a predefined group of functions (also referred to as "family of functions"). Referring to the examples set forth with respect to other drawings, stage 540 may be carried out by a fitting module such as fitting module 240.

The approximation function may be selected out of family of functions, e.g. by selecting the parameters of the function. For example, one simple family of functions is the family of parabolas of the form $y=ax^2+bx+c$. Selecting a function of this family may be implemented by determining values for the parabola parameters a, b, and c. The fitting of the approximation function may be carried out by minimizing an error estimation function, which is based on the errors (differences) between the distribution data and the selected function. For example, the error estimation function may be a least mean squared (LMS) function, and/or any other known statistical method.

An example of a distribution and an approximation function fitted thereto is given in FIG. 5, which is discussed below.

For example, the actual count of pixels in the portion of the inspection image Nactual,Di associated with each comparison value Di that was calculated may be subtracted from the (estimation) number of pixels Nestimation(Fj),Di with that comparison value Di estimated by an approximation function (Fj) from the family of functions. The results (Nestimation(Fj),Di−Nactual,Di) may be squared for each Di, and then summed to each other. That is, the error (or score) for each approximation function Fj may be Σ(Nestimation(Fj),Di−Nactual,Di)2 where the summation is for all Di. The approximation function Fj having the minimal score would be selected in such an implementation. It will be clear to a person who is skilled in the art that not all possible functions are necessarily analyzed for each set of inspection results, and that various techniques are known in the art for fitting a function to a set of results.

The family selected may depend on parameters such as the type of noise which affects the inspection of the images, the type of defects looked for, characteristics of the inspected object (e.g. patterns, etc.), and so on. For example, the family of functions described with respect to FIG. 7 was used by the inventors for fitting of inspection results in which substantially Gaussian noise (or noises) was suspected. Various implementations of the fitting which are useful in detection of defects (among other possible utilizations) are discussed below in greater detail.

The group of functions (also referred to as "family of functions") may be related to a response pattern of the inspection system. As mentioned above, the response pattern may depend on various factors, such as: beam profile, changes the beam undergo before hitting the article (described by a respective transmission function), the interaction characteristics of the article (e.g. described by a respective impulse response function), changes which the refracted/deflected beam undergo before reaching the sensor (described by a respective transmission function), and the way such outgoing signals are modified and then recorded by the sensor (e.g. described by a respective transfer function such as OTF or MTF). The group of functions may be related to any one or more of these factors.

Various groups of functions may be used, and the actual group of functions implemented may be determined by measurements of the inspection system (e.g., by measuring the beam profile) or irrespectively thereof (e.g., by selecting a set of functions which is often used for approximation, such as normal distribution). For example, the group of functions may consist of Gaussians. The family of functions may be defined e.g. based on simulations, measurements during a setup phase or during run-time, in a manual or automated manner. For example, the family of functions may be defined as described below with reference to stage 590.

Stage 550 of method 500 includes setting at least one defect detection criterion based on a result of the fitting. Referring to the examples set forth with respect to other drawings, stage 550 may be carried out by a defect detection module such as defect detection module 250. The defect detection criterion may be a threshold to which detected values (i.e. values obtained by processing of inspection data) may be compared. However, other defect detection criteria may also be implemented.

For instance, after the approximation function was fitted to the distribution, this function may be used for setting a threshold based on the selected function. The threshold may be one of the parameters of the selected functions (e.g. the constants of the function—such as a, b, c above) or another value computed based on the selected function (e.g. the zeroes of the function, its derivative at zero, and so on). In some implementations, a single threshold is computed for the entire inspection image, based on the comparison values.

However, in other implementations more than a single threshold may be computed, and applied to different pixels in the inspection image.

It is noted that the defect detection criterion may be set based on additional data, in addition to the approximation function. For example, it may further be based on an average color level of the inspection image, on its noise characteristics, and so on.

Generally, the setting of the defect detection criterion based on the result of the fitting may be used for normalization, such as by limiting the effect of a pixel associated with an outlier comparison value (e.g. large GL difference) on the defect detection settings (e.g. on the threshold).

Stage 560 of method 500 includes determining a presence of a defect in the inspection image, based on the defect detection criterion (and possibly on other parameters as well). For example, the determining of the presence of the defect may include comparing for each pixel in a portion of the inspection image (e.g., where the portion may include all the pixels of the inspection image, all pixels of a given area of the inspection image, or any other subset of pixels of the inspection image) the comparison value associated with that pixel to the threshold determined in stage 550, and if the comparison value is greater than the set threshold, determining that a defect is present in the relevant pixel. Referring to the examples set forth with respect to other drawings, stage 560 may be carried out by a defect detection module such as defect detection module 250.

For example, every pixel for which the difference of its GL from the GL of a corresponding pixel of a reference image is greater than the threshold may be classified as a possible defect, while other pixels are classified as not indicating a potential defect.

It is noted that the determining of the presence of a defect (e.g. in a selected pixel) may be a binary determination (i.e. present or non-present, defective or non-defective, and so on), but this is not necessarily so. Optionally, the determining of the presence of a defect may use a defect-indicative classification system which has more than two classes (i.e. more than just the classes of "having a possible defect" and "not having a possible defect").

Optionally, e.g., if stages 530, 540 and 550 are executed for alternative or additional reasons than defect detection, stage 550 may be followed by a stage of classifying one or more pixels of the inspection image, based on a relevant criterion set in stage 550, and optionally also based on the comparison value computed for that pixel.

Stage 560 may be followed by optional stage 570 of providing defect detection results which are based on a result of the determination of stage 560. The defect detection results may be provided in various ways (e.g. using a display, a communication interface, and so forth), and to one or more targets (e.g. to a human, to another system, and so forth). Referring to the examples set forth with respect to other drawings, stage 570 may be carried out by a defect detection module such as defect detection module 250, and/or by an output interface such as output interface 270.

Stage 560 may be followed by a stage of reporting one or more defects, if multiple pixels are processed during stage 560. The reporting may include reporting location information of at least one of the defects (and possibly of all of them) in pixel coordinates, in coordinates of the inspected article, in coordinates of a corresponding design data, etc.

The results provided may further include additional information identifying one or more defects which were identified within the inspection image, such as one or more of the following (e.g. as a part of a defect list): Location information of one or more defective pixel; Size information, indicating size of the defects; Type information, identifying initial classification of the defect; Small image excerpts of the inspection image, each of which includes one or more defective pixels; Grade of the item in one or more grading systems (e.g. indication of the likelihood of defectiveness of the indicated potential defect).

Method 500 may further include optional stage 580 of selectively applying one or more industrial processes in response to a result of the determination of the presence of the defect. Clearly, in different embodiments of the subject matter, different industrial processes may be applied. For example, stage 580 may include applying any combination of one or more of the following industrial processes: A production industrial process (e.g. further examining the inspected object, discarding the inspected object and/or another item, selecting a process which the inspected object needs to undergo, etc.); A chemical industrial process (e.g. applying to the inspected object an chemical material whose concentration is selected and/or manipulated based on the results of stage 550, etc.); A mechanical industrial process (e.g. applying mechanical force onto the inspected object, etc.); An information technology industrial process (e.g. writing information to a database and/or tangible storage, modifying communication routing channel, encrypting, etc.).

Method 500 may also continue with other actions that are based on the determined presence of the defect. For example, stage 580 may include selectively scanning areas of the inspected object in a resolution higher than the resolution of the inspection image, based on a result of stage 560. In such a case, the areas selected for further scanning may be selected based on the locations of potential defects which are classified into certain classes but not into at least one of the other classes. Referring to the examples set forth in other drawings, such inspection may be carried out by an inspection machine such as inspection machine 210, or by a posterior inspection module (which may be another inspection machine), such as posterior inspection module 280. For example, if the inspected object is indeed a wafer, the inspection image may be obtained using Electron Beam Inspection (EBI) in a first resolution, while the potential defects selected, based on the way in which they were classified, may be further inspected in much higher resolution by a Defect Review Scanning Electron Microscope (DRSEM).

Stage 580 may also include declaring the wafer (or specific dies thereof) as operational or nonoperational based on the results of stage 560 and/or the results of stage 580 (e.g. the high resolution inspection).

Inspecting only potential defects which for which a presence of a defect was determined in stage 560, while not inspecting other potential defects (e.g. received in a preliminary defects lists prior to stage 560) saves time and resources, and may also improve the results of the inspection. For example, scanning less areas of the wafer would lead to less accumulation of electrical charge resulting from the electrons beamed by the electron beam scanning apparatus.

Reverting to stage 540, it is noted that the fitting of the approximation function to the distribution data may be implemented in many ways, wherein different ways may yield best results in different scenarios. In the discussion below, two aspects of the fitting are discussed, whose implementation may improve the usability of the threshold determined based on the result of the fitting. As will be discussed below, these two aspects may be implemented separately, and in some scenarios have a synergetic effect. It is however clear that the subject matter is not restricted to these two aspects.

These two aspects are:
1. Applying a fitting which gives smaller weight to common comparison values; and
2. Applying a fitting which gives smaller weight to comparison values whose distance from an average comparison value is large.

While implementation of these two aspects is synergetic in at least some cases, for simplicity of explanation these two aspects will be discussed separately.

Figure 4:
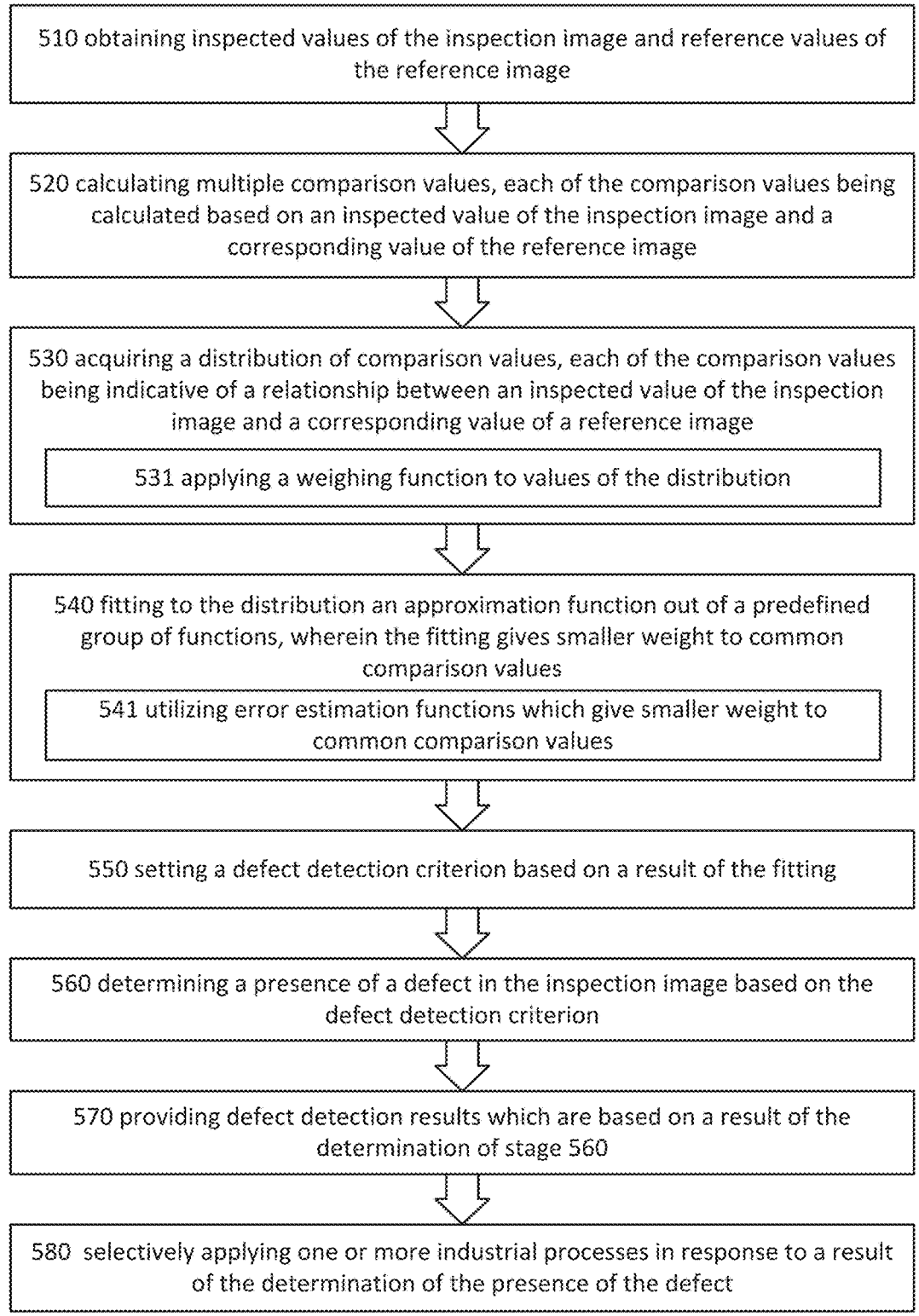

FIG. 4 illustrates method 500 according to an embodiment of the subject matter in which the fitting gives smaller weight to common comparison values. That is, stage 540 in such a case includes fitting to the distribution an approximation function out of the predefined group of functions, wherein the fitting gives smaller weight to common comparison values. It is noted that the term "common comparison values" is used to refer to comparison values of relatively frequent occurrence (i.e., when compared to the frequency of appearance of other comparison values).

Figure 5:
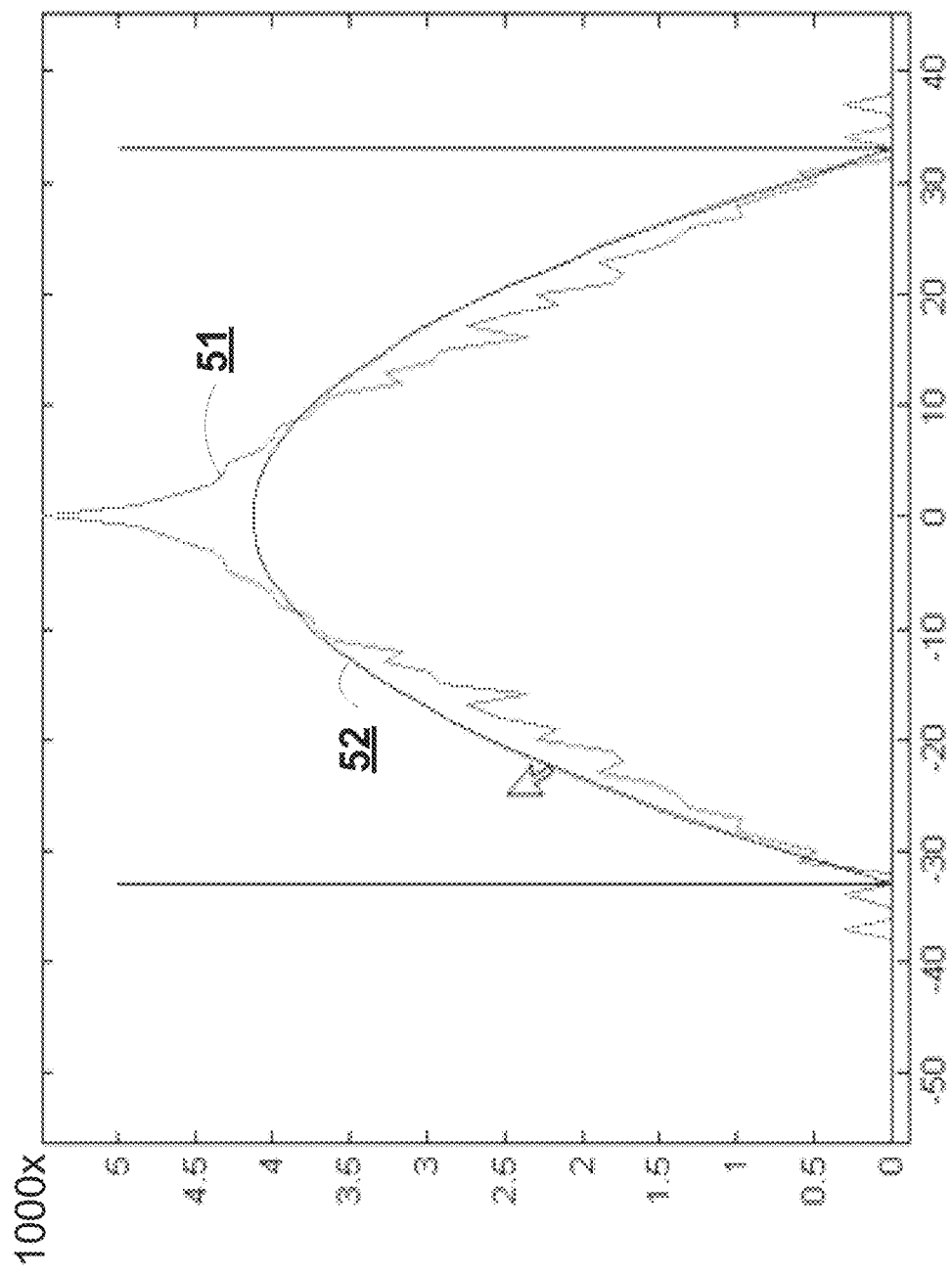
FIG. 5 illustrates a distribution and an approximation function fitted thereto, according to an embodiment of the subject matter.

Referring to distribution 51 which is illustrated in FIG. 5, it is noted that the abscissa represents numeral differences between color values of pixels of the inspection image to color values of pixels of the reference image, and that the ordinate represents a calibrated number of occurrences (in this case, the number of occurrences is logged, as will be discussed below in greater detail). Clearly, there are more occurrences of pixels for which the difference is zero or near zero than there are occurrences for which the difference is larger than 30. The former are therefore more common than the latter.

Two of the ways in which such fitting may be implemented (together or independently) are:
1. Applying a weighting process (e.g. an operator) to the distribution data before it is fitted to one of the model functions of the family; and
2. Utilizing an error estimation function which gives smaller weight to common comparison values.

Referring to the first alternative, the method may include applying a weighting process to the amount of occurrences for various possible comparison values (e.g., difference values).

FIG. 5 illustrates distribution 51, and approximation function 52 fitted thereto, according to an embodiment of the subject matter. In the example illustrated in FIG. 5, a logarithm operation (hereinafter also "log") was applied to the distribution values obtained for all of the pixels of an exemplary image generated by inspection of a wafer part (illustrated by the line 51). Line 51 shows for each difference value (illustrated along the abscissa) the calibrated logarithm of the total number of pixel pairs having that difference in a comparison of the reference image and the inspection image (the calibrated logarithms are represented by the ordinate). All the log values are of logarithms of the same base.

Assuming a model of white noise which is ideally reflected by a Gaussian in the original histogram (the original distribution of differences, before it was logged), the distribution may then be approximated by a parabola (which is a result of logging a Gaussian). The fitted approximation function 52 in the illustrated example is a parabola.

It is noted that the applying of the operator, if implemented, is executed during the acquiring of stage 530. That is, stage 530 may include stage 531 of applying an operator to values of the distribution. For example, stage 531 may include logging the values of the distribution. In some implementations it may be desirable to use an operator which is somewhat different than a simple log.

For example, the operator applied in stage 531 may be such that for at least half of values of the distribution, a difference between an output value of the operator and an output value of a given log function is less than 10% of a maximum value of the distribution.

For example, the operator applied in stage 531 may be such that for at least half of values of the distribution, a difference between an output value of the operator (for a selected value out of the at least half of the values of the distribution) and a result of a maximum function whose inputs are: (a) an output value of a log function (applied to the selected value), and (b) a constant value, is less than 10% of a maximum value of the distribution.

For example, the operator applied in stage 531 may be such that for at least half of values of the distribution, a difference between an output value of the operator W(x) (for a selected value x) and MAX(log(x), const) is less than 10% of a maximum value of the distribution. For example, the constant const may be equal to zero (const=0).

While operators such as logarithm or rooting may be implemented for giving smaller weight to common comparison values, giving smaller weight to common comparison values may also be facilitated by utilizing error estimation functions which gives smaller weight to common comparison values (denoted stage 541). For example, instead of $\Sigma(\text{Nestimation}(F_j), D_i - \text{Nactual}, D_i)2$ as suggested above, the error estimation function (which is later minimized) may be $\Sigma(1/\text{Nestimation}(F_j), D_i) \cdot (\text{Nestimation}(F_j), D_i - \text{Nactual}, D_i)2$.

Giving less emphasis to common comparison values may be useful, for example, when the variations in the number of occurrences between different comparison values in the distribution are significant. For example, if more than 60% of the differences are divided between, for example, just 11 values (e.g., for a difference −5 to difference +5), the impact of the rest of the difference on the fitted function may be too small for some uses. Logging (or otherwise weighting) the distribution values in such an example would lower the relative portion of these 11 difference values to significantly below 60%.

Figure 6:
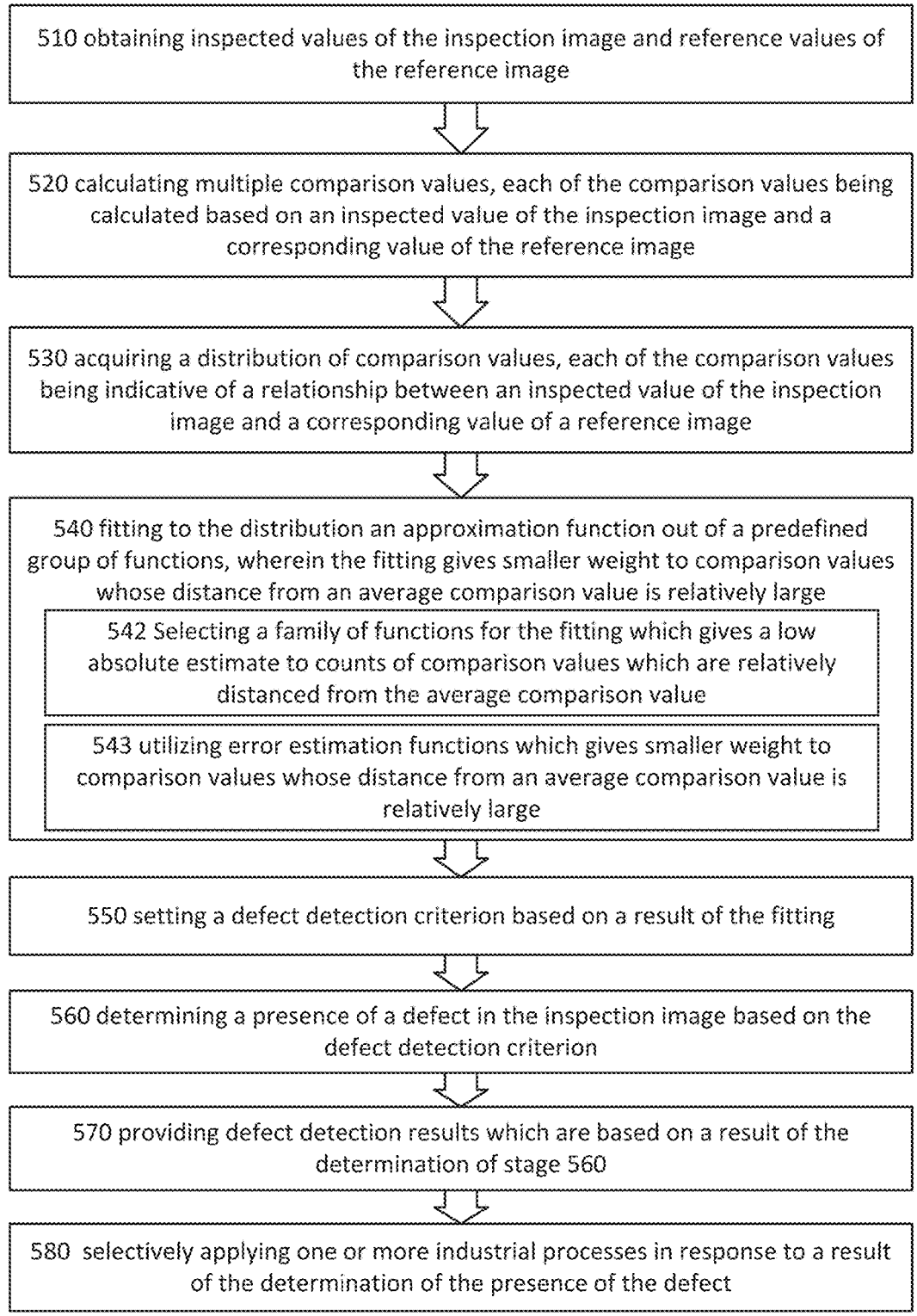

FIG. 6 illustrates method 500 according to an embodiment of the subject matter in which the fitting gives smaller weight to comparison values whose distance from an average comparison value is relatively large. For example, the stage 540 may include fitting to the distribution an approximation function out of a predefined group of functions, wherein the fitting gives smaller weight to comparison values whose distance from an average comparison value is larger than a threshold (e.g. larger than a standard deviation of the distribution). It is noted that optionally the threshold may be a predetermined threshold, but this is not necessarily so.

Figure 7:
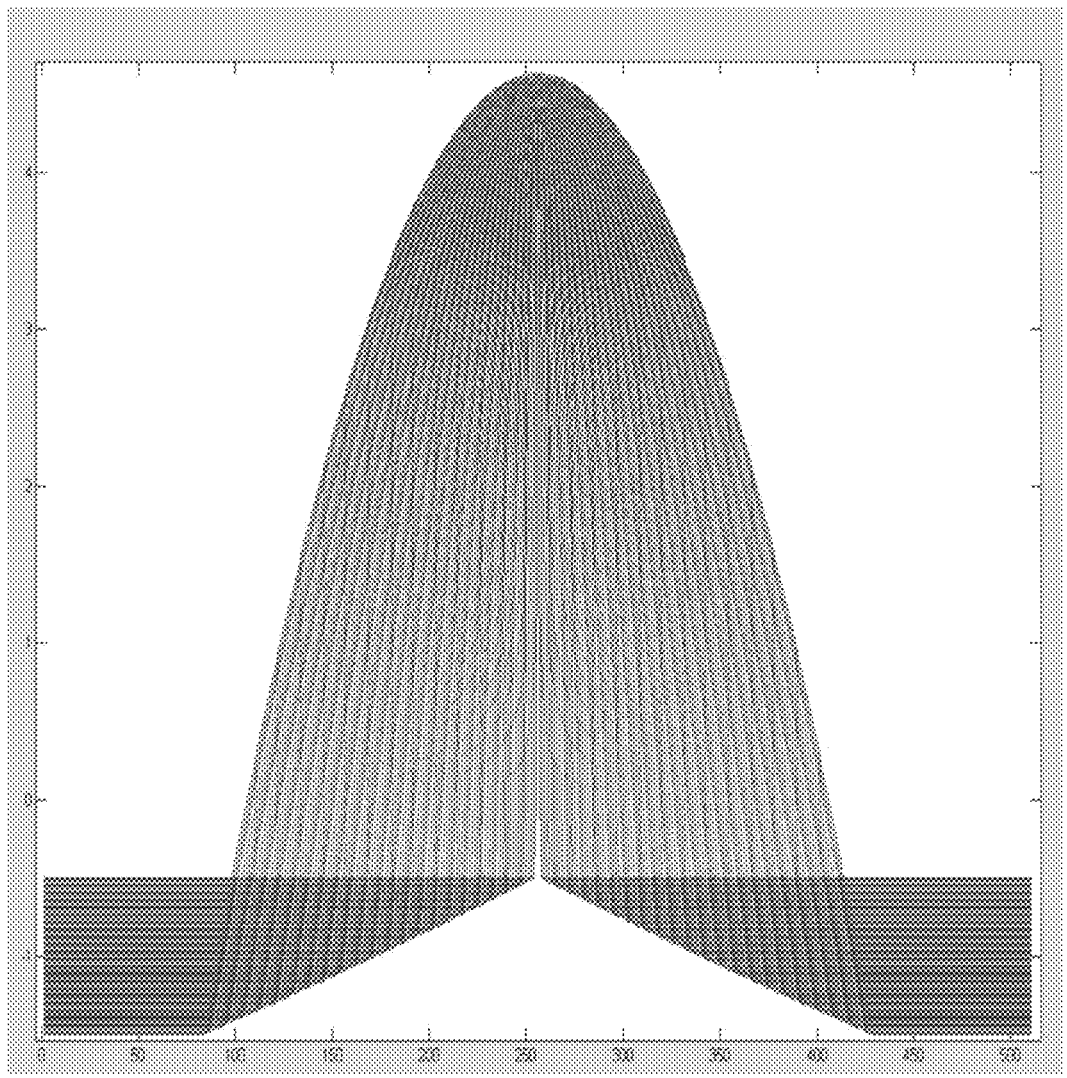
FIG. 7 illustrates a family of functions out of which an approximation function may be fitted to a distribution, according to an embodiment of the subject matter.

For example, FIG. 7 illustrates such a family of functions, wherein each of the functions of the family is a continuous function which gives a constant value below a lower-threshold and above a higher-threshold, and between those thresholds the function is equal to a parabola. The parameters of the function which differentiate it from other functions of the family may be, for example, the parameters of the parabola and the constant value. It is noted that these parameters may be interdependent (e.g., both the width of the parabolic part of the function and the thresholds may be derived from a single parameter q).

Figure 8A:
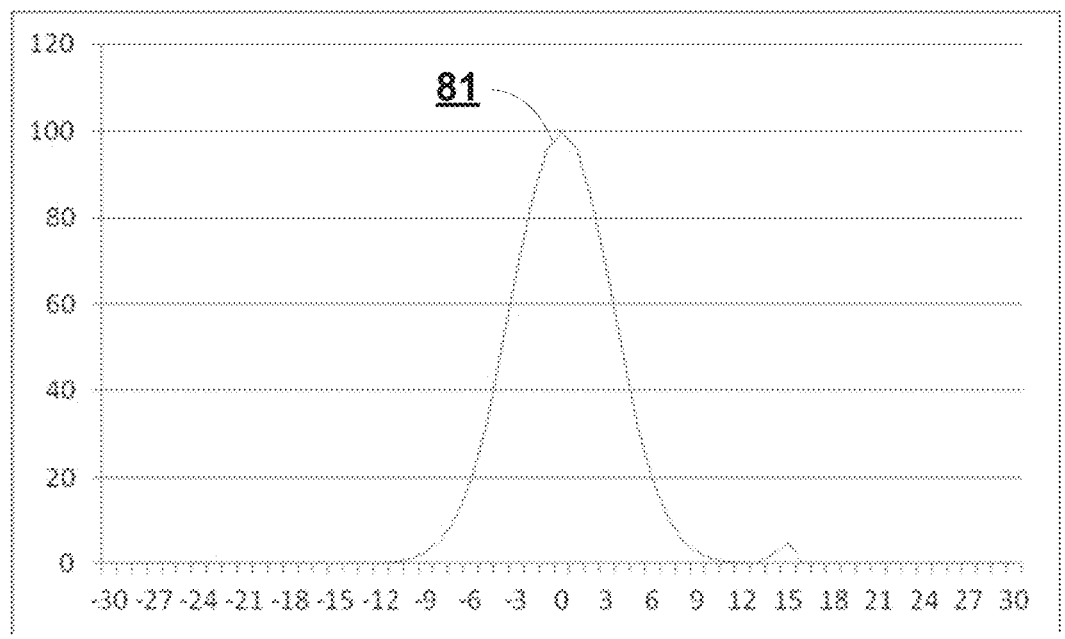
FIG. 8A illustrates a distribution which is acquired by comparing pixels of an inspection image in which a defective part of the article is imaged to pixels of a reference image which do not include such a defect, according to an embodiment of the subject matter.
Figure 8B:
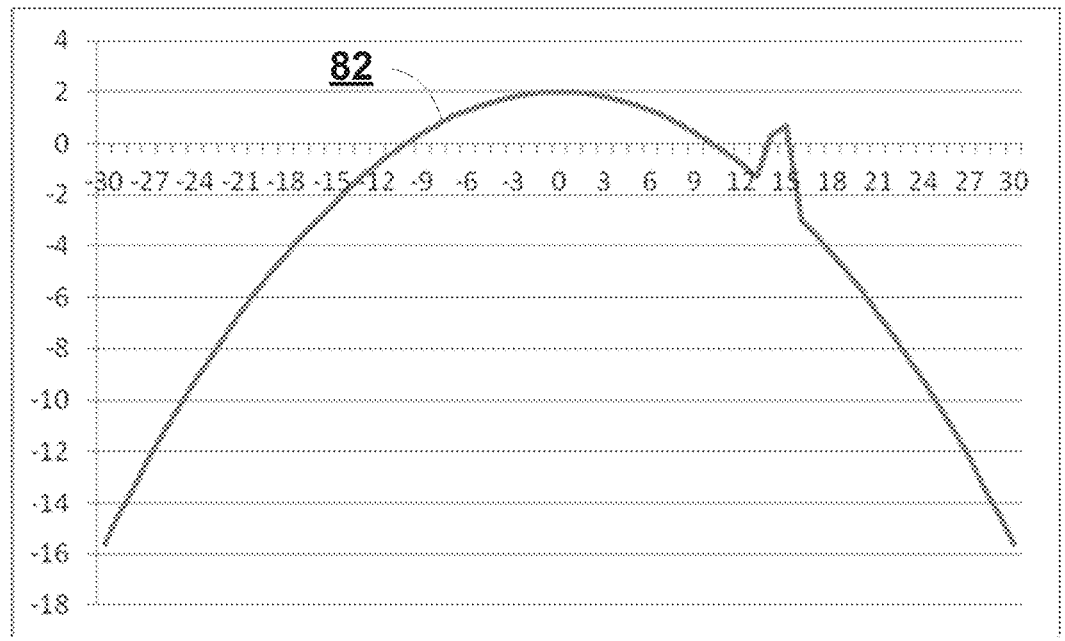
FIG. 8B illustrates a distribution which is a log of the distribution of FIG. 8A, according to an embodiment of the subject matter.

FIG. 8A illustrates distribution 81 which is acquired by comparing pixels of an inspection image in which a defective part of the article is imaged to pixels of a reference image which do not include such a defect. Distribution 82 illustrated in FIG. 8B is a log of distribution 81.

Giving smaller weight to comparison values whose distance from an average comparison value is large is useful for example for giving less weight to defects. Naturally, defects are manifested many a time by pixels whose color value greatly differs from that of the corresponding reference pixels (which is assumingly non-defective). Therefore, such defects are reflected in the distribution as positive counts of pixels in a difference level which is quite remote from the average difference level.

In the example of FIG. 8A this is represented by the peak around comparison value of 15 (e.g. a difference of 15 gray levels). An attempting to fit the graph of FIG. 8A to a regular Gaussian would yield a Gaussian which is unnecessarily wide—because relatively large weight would be given to the defect of difference 15. This is even more apparent after the logging operation discussed above, as reflected by FIG. 5B.

Applying a fitting which gives smaller weight to difference values whose distance from an average difference value is large may be implemented in various ways. Two of the ways in which such a fitting may be implemented (together or independently) are:
1. Selecting a family of functions for the fitting which gives a low absolute estimate to counts of comparison values which are relatively distanced from the average comparison value (e.g., as exemplified in FIG. 7). This is denoted as stage 542. It is noted that such selecting (as any selection of the family of functions) may be executed before the acquiring of the inspection image and may be irrespective thereof.
2. Utilizing an error estimation function which gives smaller weight to difference values whose distance from an average difference value is relatively large (e.g. larger than the standard deviation). This stage is denoted stage 543. For example, instead of $\Sigma(N_{estimation(Fj),Di} - N_{actual,Di})^2$ as suggested above, the error estimation function (which is later minimized) may be $\Sigma(1/Di) \cdot (N_{estimation(Fj),Di} - N_{actual,Di})^2$.

In the example of FIG. 7, in each of the functions of the family of functions used for the fitting, the function gives a constant value below a lower-threshold and above a higher-threshold. However, in other variations the functions would give outputs which are not constant, but which are nevertheless bound and relatively small. For example, the fitting may include fitting to the distribution an approximation function whose outputs for comparison values whose distance from the average comparison value is larger than a threshold (e.g. larger than the standard deviation of the distribution) are bound between a higher limit and a lower limit, so that the difference between the higher and lower limits is smaller than 5% of the maximum value of the distribution. This may prove to be especially useful when combined together with logging.

It is noted that the variations discussed with respect to FIGS. 5 and 6 may be implemented together, wherein the fitting gives smaller weight to: (a) common comparison values, and to (b) comparison values whose distance from an average comparison value is larger than a threshold (e.g. larger than a standard deviation of the distribution). It is noted that optionally the threshold may be a predetermined threshold, but this is not necessarily so. Implementing a fitting which combines these two aspects (e.g. as may be implemented with respect to the family of functions shown in FIG. 7) may achieve synergetic results.

Fitting which gives smaller weight to: (a) common comparison values, and/or to (b) comparison values whose distance from an average comparison value is larger than a threshold, e.g., as discussed above, may be implemented, for example, for reaching a predetermined false alarm ratio when processing the inspection image (and the reference image) for detecting defects therein. This way, out of all the compared pixels, only a subset of pixels whose size is bound (i.e., equal or possibly smaller than) the predetermined false alarm ratio will comply with the set defect detection criterion (e.g. would have a difference which exceeds a threshold which is determined according to the techniques above). This may be useful, for example, if the processing of each pixel in which a presence of a defect is detected requires significant time, computation power and/or other resources.

In its different possible implementations, method 500 (as well as system 200 discussed below) may be used for any one of the following reasons, among others: high correlation to the residual noise in the block; increase stability; increase sensitivity; keep constant false alarm ratio in different inspection images.

FIG. 9 is a flow chart of computerized method 500 for computerized detection of defects in an inspected object, according to an embodiment of the subject matter. The stages which are illustrated in FIG. 9 but not in FIG. 3 are optional, and the different possible combinations of those stages and of stages illustrated in FIG. 3 may be implemented in different embodiments of the subject matter.

Method 500 may include stage 502 of scanning an area of the inspected article (e.g. the wafer) to provide scanned image data. The scanning of the scanned area may be a part of larger parts of the wafer—e.g. a die, multiple dies, or even the entire wafer (or at least the parts which include electronic circuit parts). The scanning may be carried out by using different techniques such as electron beam scanning and optical scanning. Referring to the examples set forth in other drawings, stage 502 may be carried out by any scanning, imaging and/or detecting apparatus such as inspection machine 210.

An implementation of the scanning of stage 502 for scanning a wafer may include, for example, the following substeps: (a) illuminating an inspected die; (b) receiving detection signals by at least one detector; (c) processing the detection signals to provide an image of a portion of the illuminated die, the image includes a grid of pixels, each characterized by a signal such as a gray level signal; and optionally (d) selecting which pixel out of the grid of pixels to currently process, said pixel being the selected pixel. The selection may follow a predefined pattern, such as a raster scan pattern, but other selection schemes may be implemented.

Since the scanning may be a lengthy process, some or all of the other stages (e.g. any one or more of stages 510 through 560) may be carried out at least partly concurrently with the scanning of one or more parts of the inspected article, such as the scanning of the scanned area of the inspected article in stage 502. Alternatively, stage 502 may entirely precede stage 510, and possibly other stages of method 500 (e.g. stages 520, 530, 550, 560). The scanned image data (or part thereof) may be processed in order to determine the inspected value and the reference values obtained in stage 510. The scanned image data and/or the inspected value and the reference value may be stored in a database which is stored in a tangible memory, whether volatile (e.g. DRAM, SRAM) and/or non-volatile (e.g. Hard-drive, Flash memory).

Method 500 may further include additional stages that precede the optional scanning of the scanned area in stage 502, such as wafer alignment and translation of the wafer so that the reference area may be scanned. The global alignment of the wafer (e.g. by aligning a stage on which the wafer is positioned) may be based, for example, on CAD data, using coarse anchor points from the design data. For example, coarse registration on a single large target by the Applied Materials patented RGA algorithm may be implemented. The translation of the wafer may include translating the wafer to a position in which the reference die may be scanned. Alignment methods are known in the art. An illustration of a method for such an alignment is described in U.S. Pat. Nos. 5,699,447, 5,982,921 and 6,178,257B1 of Alumot. Another alignment method is described at U.S. Pat. No. 5,659,172 of Wagner.

The information required for successful execution of such preliminary stages may be retrieved from a previously determined recipe (or recipe parameters) and/or from a configuration file (referred to as "config") which does not pertain to a specific scan or to a specific layer of a wafer, but rather to a configuration of the scanning machine executed immediately after its manufacture (or at a later time, irrespective of any specific target to be scanned).

Method 500 may also include stage 590 of defining the family of functions. Stage 590 may be executed based on the results of a stage of measuring at least one parameter of the inspection process and/or of the inspection system (e.g. measuring a noise indicative parameter of the inspection system), but this is not necessarily so.

Method 500 may also include defining the family of functions based on a processing of collected signals arriving from a group of articles comprising at least one reference article other than the article. Such reference articles may include, for example, parts of known dimensions (and possibly also of known geometry), and may be used to calibrate the system which executes method 500, by defining the family of functions according to the inspection results of the reference articles. It is noted that a combination of these two may also be used—measuring parameters of the inspection system and/or of the inspection process, and selecting a family of functions based on the results.

Referring to method 500 generally, it is noted that since method 500 is a computerized method, a program of instructions may be implemented, which, when executed by one or more processors, results in the execution of one of the aforementioned variations of method 500.

It would be clear to a person who is of skill in the art that instructions may be included in the program of instructions for executing some or all of the stages of method 500 (in all possible combinations suggested above), even if the inclusion of such instructions has not been explicitly elaborated.

Referring to method 500, it will be understood that method 500 may be implemented by a system which is a suitably programmed computer. Likewise, a computer program may be implemented, being readable by a computer for executing any variation of method 500 discussed above. A machine-readable memory may be implemented, tangibly embodying a program of instructions executable by the machine for executing any variation of method 500 discussed above.

For example, a non-volatile program storage device that is readable by machine may be implemented, tangibly embodying a program of instructions executable by the machine to perform a method for defect detection in an inspection image generated by collecting signals arriving from an article comprising the steps of: (a) acquiring a distribution of comparison values, each of the comparison values being indicative of a relationship between a value associated with a pixel of the inspection image and a corresponding reference value; (b) fitting to the distribution an approximation function out of a predefined group of functions; (c) setting a defect detection criterion based on a result of the fitting; and (d) determining a presence of a defect in the inspection image, based on the defect detection criterion.

Optionally, the approximation function is a Parabola and the fitting includes selecting one or more Parabola parameters.

Optionally, the fitting includes selecting the approximation function by estimating errors between the distribution of comparison values and the approximation function.

Optionally, the fitting gives smaller weight to common comparison values.

Optionally, the acquiring comprises applying an operator to values of the distribution, wherein for at least half of values of the distribution, a difference between an output value of the operator and $MAX(\log(x), \text{const})$ is less than 10% of a maximum value of the distribution.

Optionally, the fitting gives smaller weight to comparison values whose distance from an average comparison value is larger than a standard deviation of the distribution.

Optionally, the fitting gives smaller weight to: (a) common comparison values, and to (b) comparison values whose distance from an average comparison value is larger than a standard deviation of the distribution.

While certain features of the subject matter have been illustrated and described herein, many modifications, substitutions, changes, and equivalents will now occur to those of ordinary skill in the art. It is, therefore, to be understood that the appended claims are intended to cover all such modifications and changes as fall within the true spirit of the subject matter.

It will be appreciated that the embodiments described above are cited by way of example, and various features thereof and combinations of these features can be varied and modified.

While various embodiments have been shown and described, it will be understood that there is no intent to limit the subject matter by such disclosure, but rather, it is intended to cover all modifications and alternate constructions falling within the scope of the subject matter, as defined in the appended claims.

What is claimed is:

1. A method for computerized defect detection in an inspection image generated by collecting signals arriving from an article, the method comprising:
    acquiring a distribution of comparison values, each of the comparison values being indicative of a relationship between a value associated with a pixel of the inspection image and a corresponding reference value;
    selecting a family of functions, from a plurality of families of functions, based on a noise characteristic of an inspection of the article and a type of defect to be detected;
    selecting an approximation function from the selected family of functions;
    fitting, to the distribution, the approximation function that is selected from the family of functions;
    setting a defect detection criterion based on a result of the fitting; and determining, by a processing device, a presence of a defect in the inspection image based on the defect detection criterion.

2. The method according to claim 1, wherein the approximation function is a Parabola and the fitting includes selecting one or more Parabola parameters.

3. The method according to claim 1, wherein the fitting includes selecting the approximation function by estimating errors between the distribution of comparison values and the approximation function.

4. The method according to claim 1, wherein each of the comparison values is indicative of a difference between a color value of a pixel of the inspection image and a color value of a corresponding pixel of a reference image.

5. The method according to claim 1, wherein the fitting gives smaller weight to common comparison values.

6. The method according to claim 1, wherein the acquiring comprises applying an operator to values of the distribution, wherein for at least half of the values of the distribution, a difference between an output value of the operator and a maximum function is less than 10% of a maximum value of the distribution, wherein the maximum function is based on another output value of a logarithmic function and a constant value.

7. The method according to claim 1, wherein the fitting gives smaller weight to comparison values whose distance from an average comparison value is larger than a standard deviation of the distribution.

8. The method according to claim 1, wherein the fitting gives smaller weight to: (a) common comparison values, and to (b) comparison values whose distance from an average comparison value is larger than a standard deviation of the distribution.

9. A system configured to detect defects in an inspection image generated by collecting signals arriving from an article, the system comprising:
a memory; and
a processor, operatively coupled with the memory, to:
acquire a distribution of comparison values, each of the comparison values being indicative of a relationship between a value associated with a pixel of the inspection image and a corresponding reference value;
select a family of functions, from a plurality of families of functions, based on a noise characteristic of an inspection of the article and a type of defect to be detected;
select an approximation function from the selected family of functions;
fit, to the distribution, the approximation function that is selected from the family of functions;
set a defect detection criterion based on a result of the fitting; and determine a presence of a defect in the inspection image based on the defect detection criterion.

10. The system according to claim 9, wherein the approximation function is a Parabola and the fitting includes selecting one or more Parabola parameters.

11. The system according to claim 9, wherein the processor is further to select the approximation function by estimating errors between the distribution of comparison values and the approximation function.

12. The system according to claim 9, wherein each of the comparison values is indicative of a difference between a color value of a pixel of the inspection image and a color value of a corresponding pixel of a reference image.

13. The system according to claim 9, wherein the processor is further to give smaller weight to common comparison values when fitting the approximation function to the distribution.

14. The system according to claim 9, wherein the processor is further to apply an operator to values of the distribution, wherein for at least half of the values of the distribution, a difference between an output value of the operator and a maximum function is less than 10% of a maximum value of the distribution, wherein the maximum function is based on another output value of a logarithmic function and a constant value.

15. The system according to claim 9, wherein the processor is further to give smaller weight to comparison values whose distance from an average comparison value is larger than a standard deviation of the distribution when fitting the approximation function to the distribution.

16. The system according to claim 9, wherein the processor is further to give smaller weight to: (a) common comparison values, and to (b) comparison values whose distance from an average comparison value is larger than a standard deviation of the distribution, when fitting the approximation function to the distribution.

17. A non-transitory computer readable storage medium having instructions that, when executed by a processing device, cause the processing device to perform operations for defect detection in an inspection image generated by collecting signals arriving from an article, the operations comprising:
acquiring a distribution of comparison values, each of the comparison values being indicative of a relationship between a value associated with a pixel of the inspection image and a corresponding reference value;
selecting a family of functions, from a plurality of families of functions, based on a noise characteristic of an inspection of the article and a type of defect to be detected;
selecting an approximation function from the selected family of functions;
fitting, to the distribution, the approximation function that is selected from the family of functions;
setting a defect detection criterion based on a result of the fitting; and determining a presence of a defect in the inspection image based on the defect detection criterion.

18. The non-transitory computer readable storage medium according to claim 17, wherein the approximation function is a Parabola and the fitting includes selecting one or more Parabola parameters.

19. The non-transitory computer readable storage medium according to claim 17, wherein the fitting includes selecting the approximation function by estimating errors between the distribution of comparison values and the approximation function.

20. The non-transitory computer readable storage medium according to claim 17, wherein the fitting gives smaller weight to common comparison values.

21. The non-transitory computer readable storage medium according to claim 17, wherein the acquiring comprises applying an operator to values of the distribution,
wherein for at least half of the values of the distribution, a difference between an output value of the operator and a maximum function is less than 10% of a maximum value of the distribution, wherein the maximum function is based on another output value of a logarithmic function and a constant value.

22. The non-transitory computer readable storage medium according to claim 17, wherein the fitting gives smaller weight to comparison values whose distance from an average comparison value is larger than a standard deviation of the distribution.

23. The non-transitory computer readable storage medium according to claim 17, wherein the fitting gives smaller weight to: (a) common comparison values, and to (b) comparison values whose distance from an average comparison value is larger than a standard deviation of the distribution.

\* \* \* \* \*